(12) United States Patent
Horn

(10) Patent No.: US 6,379,314 B1
(45) Date of Patent: Apr. 30, 2002

(54) INTERNET SYSTEM FOR TESTING HEARING

(75) Inventor: Gerald Horn, Deerfield, IL (US)

(73) Assignee: Health Performance, Inc., Oak Forest, IL (US)

( * ) Notice: Subject to any disclaimer, the term of this patent is extended or adjusted under 35 U.S.C. 154(b) by 29 days.

(21) Appl. No.: 09/596,940

(22) Filed: Jun. 19, 2000

(51) Int. Cl.[7] .................................................. A61B 5/00

(52) U.S. Cl. ......................................... 600/559; 73/585

(58) Field of Search ............................... 600/300, 559; 73/585; 381/124

(56) References Cited

U.S. PATENT DOCUMENTS

| | | | | |
|---|---|---|---|---|
| 4,157,456 A | | 6/1979 | Voss | 73/585 |
| 4,284,847 A | | 8/1981 | Besserman | 73/585 |
| 4,489,610 A | | 12/1984 | Slavin | 73/585 |
| 4,759,070 A | | 7/1988 | Voroba et al. | 381/60 |
| 4,961,230 A | | 10/1990 | Rising | 381/323 |
| 4,989,251 A | | 1/1991 | Mangold | 381/314 |
| 5,916,174 A | * | 6/1999 | Dolphin | 600/559 |
| 5,928,160 A | * | 7/1999 | Clark et al. | 600/559 |
| 6,022,315 A | * | 2/2000 | Iliff | 600/559 |
| 6,086,541 A | * | 7/2000 | Rho | 600/559 |

FOREIGN PATENT DOCUMENTS

| | | | | |
|---|---|---|---|---|
| WO | WO 00/64350 | * | 2/2000 | 600/559 |

OTHER PUBLICATIONS

"AAI's Online Hearing Test," Audiology Associates Incorporated, Sep. 5, 1999.*
"Online Hearing Test," Handtronix, Mar. 4, 1997.*
FreeHearing Test.com, (2000).*

* cited by examiner

Primary Examiner—Kevin Shaver
Assistant Examiner—Charles Marmor, II
(74) Attorney, Agent, or Firm—Karl Bozicevic; Bozicevic, Field & Francis LLP

(57) ABSTRACT

A method of allowing a community of users to self-administer a hearing test via a computer system accessed over the Internet is disclosed. A web site is generated which is accessible by a community of users over the Internet. The web site presents a screen to a user which gives instructions on responding to sounds. Electronic data is sent to users which instructs the user's computer to generate a series of sounds at different amplitudes and frequencies. The user blocks sound to one ear and responds to sounds detected by the other ear. The responses are analyzed against a known standard to provide information on user hearing.

1 Claim, No Drawings

INTERNET SYSTEM FOR TESTING HEARING

FIELD OF THE INVENTION

This invention relates generally to the field of medical tests and specifically to hearing tests. More specifically the invention relates to a self-administered hearing test provided over the Internet.

BACKGROUND OF THE INVENTION

Hearing loss can occur at all ages. Causes include environmental, such as from repetitive exposure to very loud music or other external noise; medical, including that caused by nerve damage, tumor or drug toxicity; genetic; and injury, such as may occur from rupture of the tympanic membrane of the ear. A major challenge in treating hearing loss is early identification. Conventional hearing testing generally requires sophisticated equipment, or testing at dedicated centers by experienced personnel.

The use of audiometric instruments in the screening and characterizing of human hearing is commonly found in schools, clinics, and in the offices of hearing aid dispensing professionals. Audiometric instruments employ pure tones, speech, and other stimuli that are within the audible range of human hearing. These sounds are delivered to the ear vicinity through transducers that are attached to the output portion of the audiometry instrument via cables.

Sound can be delivered to the ear by air-conduction transducers, such as supra-aural earphones housed in headsets, through bone-conduction transducers which make direct contact with the temporal bone area located immediately behind the ear, or by other means. Specifications and calibration standards for audiometers are available from agencies such as the American National Standards Institute (ANSI) which also provide a basis for classifications of audiometry instruments.

Recently available computer-based audiometric instruments are employed to facilitate testing procedures and improve patient records management. Automatic audiometers are becoming widely accepted in hearing screening applications such as in schools and industrial clinics. This automated process approach results in minimal operator involvement, faster testing, and in some instances improved accuracy.

Portable versions of automatic audiometry instruments incorporate microprocessors and miniature electronic components with innovative packaging and manufacturing technology to produce compact and light weight instruments suitable for most portable applications. While the cost and size of electronic components continue to decline, audiometry instruments still have at least two basic system components: a desk top electronic module connected via a cable to a separate standardized headset module to be worn on the patient's head.

Slavin, U.S. Pat. No. 4,489,610, discloses the major elements of a computerized audiometer which may be operated automatically or by a technician. The device is housed in a cabinet which contains keyboard, printer and display devices. The apparatus disclosed also includes tone generator circuits, tape recorder based audible instruction generator, central processing unit, Read Only Memory (ROM) for storage of software, Random Access Memory (RAM) for storage of diagnostic data, and further includes a programming output port for coupling to a programmable hearing aid. Other options include interface ports to connect with a modem, remote printer, and data storage devices. Similar to all other audiometry instruments, the Slavin computerized audiometer has a patient operated switch in addition to cable connected transducers (headset) to be worn by the patient.

Besserman, U.S. Pat. No. 4,284,847, discloses an audiometry apparatus which is microprocessor-based. The apparatus includes tone generation means with variable frequency and intensities, various memory elements for software and patient data storage, a key-board, and a display device. The apparatus has interface capabilities with remote computers for data transfer. One of the main features of the invention is the ability to compare recent audiogram data with previously acquired ones and automatically compute hearing threshold shifts.

U.S. Pat. No. 4,157,456 to Voss discloses an audiometric testing system having earphones, a patient feedback switch, a tone generation means which is controlled for both frequency and loudness, a memory for storage of diagnostic data, and data output means.

Voroba et al., U.S. Pat. No. 4,759,070, teach a patient controlled hearing test instrument with hearing aid programming capabilities. The system referred to as "master hearing aid" has both an operator and patient's console. Both consoles are microprocessor based. The patient is presented with stimuli and using the provided console which is electrically attached to a patient-worn hearing aid via a cable, the patient can optimize hearing aid characteristics in terms of amplification and other performance characteristics. The system comprises a number of physical units, including four loudspeakers for environmental noise simulation. All units are interconnected by means of cabling. The stimuli are generated by standard tone generators, tape recorded background sounds, and verbal instructions to the patient.

U.S. Pat. No. 4,989,251 to Mangold teaches a hearing aid programming method, and U.S. Pat. No. 4,961,230 to Rising teaches a hearing aid programming interface method having a battery compartment adapted to hold a coupler member for connection to an external programming device.

It is well known in the hearing diagnostic field that even though improvements in the reliability of transducer cabling continues, damage to the cabling and contact terminals remains to be a major problem. This failure leads to intermittent dysfunction which may lead to noisy and erratic sound transmission and possibly erroneous patient diagnosis. Even if the cabling damage is promptly detected, the audiometer must remain inoperable until a replacement or a repaired headset arrives.

Another disadvantage of the cabling associated with the present two-piece audiometer systems involves the limited mobility imposed on the patient wearing the headset who must remain close to the attached base instrument. Even the most portable types of audiometry instruments presently on the market impose a penalty on both the clinician who has to provide desk space to operate or store the audiometer and the associated headset and the patient who has to deal with cables which may get tangled with other cables and instruments in the clinical setup. This is particularly problematic with active children who have the tendency to move around and displace the critical placement of the headset on the ear.

Another less obvious but very significant disadvantage of the present desk-top or lap-top audiometer approaches involves the size reduction limitation imposed by the two-piece design. Although it may seem desirable and technically conceivable to make the audiometer extremely small and light weight using very large scale integration (VLSI)

technologies, functionally it is highly undesirable because of the potential for the base instrument to be pulled and moved by the headset cable as the patient moves. Not only may this motion cause the instrument to drop and possibly break but this motion will also cause mechanical movements of the instrument to become acoustically coupled to the patient resulting in interference with the on-going tests and possibly invalidating threshold measurements. For this reason, most presently available audiometry instruments must maintain a minimum size and weight to stabilize the instrument while in operation.

SUMMARY OF THE INVENTION

A computer system is disclosed which is accessible to a community of users over the Internet. The system presents a screen or series of screens to users which (1) prompt the user to enter information such as user name and age, and (2) instructs the user on how to respond to sounds generated as a result of data sent to a user's computer. A series of sounds at different frequencies and amplitudes are generated while the user blocks sound from reaching one ear and responds to sound detected such as by clicking a computer mouse or pressing a key on the keyboard. The system analyzes the responses relative to factors such as the user age and provides results to the user on the users hearing.

An aspect of the invention is that the hearing test can be self-administered.

Another aspect of the invention is that the test can be widely and economically distributed over the internet.

An advantage of the invention is that it does not require the use of expensive equipment.

A feature of the invention is that it can provide results to a user and/or the user's caregiver in real time.

An object of the invention is to make a simple, low-cost, accurate hearing test available to users over the internet.

These and other aspects, objects, features and advantages will become apparent to those skilled in the art upon reading this disclosure.

DETAILED DESCRIPTION OF PREFERRED EMBODIMENTS

Before the present web site, system and method are described, it is to be understood that this invention is not limited to the particular tests, symbols and steps described, as such may, of course, vary. It is also to be understood that the terminology used herein is for the purpose of describing particular embodiments only, and is not intended to be limiting, since the scope of the present invention will be limited only by the appended claims.

It must be noted that as used herein and in the appended claims, the singular forms "a", "and," and "the" include plural referents unless the context clearly dictates otherwise. Thus, for example, reference to "a test" includes a plurality of tests and reference to "the sound " includes reference to a number of sounds, and equivalents thereof known to those skilled in the art, and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference in their entirety, and specifically to disclose and describe the methods and/or materials in connection with which the publications are cited.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

The abbreviation TOV1 means a table of values 1 or a table of test values 1. The TOV can be generated by a range of methods and may involve testing groups of individuals in a given age range. The individuals are preferably normal hearing individuals who are audimetrically tested at frequencies in a range of 500–12,000 hz.

The abbreviation HL means hearing level.

The abbreviation OdB HL means a point just below which an individual can barely detect a sound.

The abbreviation BACS means background audio contrast stimulus.

ELEMENTS OF THE TESTING SYSTEM

1. Download system compatibility with PC's and Windows 95 and above operating systems. Online system compatibility cross-platform. Volume control set to high pretesting.
2. Using simple sound attenuation provided by secure coverage of one ear and or the outer ear canal, the "open" or "receiving" ear is tested.
3. A background noise "probe" is first presented to the "open" or "receiving" ear with adjustable volume control. The test subject adjusts a volume control slide to a point where the continuous probe sound can barely be heard. A series of iterative adjustments further refine this point, further known as the system baseline sound level (SBS).
4. A series of pure tones are presented at time durations that may range from about 50 msec to continuous, though shorter time frames are preferred. The frequency of the presented tone varies from 250–12,000 Hz, where each tone is selected according to a table of values (TOV).
5. Creation of the TOV Patients with completely normal hearing for age, as verified by AC (air conduction) and BC (bone conduction) audiometry are tested groups stratified into 5 yr increments from age 25, with sufficient numbers for statistical significance of data in each group. 5 PC systems, encompassing the 5 most commonly used sound cards available US (3) and worldwide (2) are used on each patient tested. The duration of each pure tone is determined in a separate study and kept uniform throughout this testing phase. During this study the decibel level is tested in 10 dB increments to 120 dB for each frequency tested until consecutive responses are elicited.

A TOV 'raw data' is created for each sound card for frequency vs. age using the SBS and dB relative to the SBS as the data values recorded. From the TOV 'raw data' a TOV 'test table final' is derived, with a determination made based on % availability of cards, and cross platform validity of data from card to card. This data is defined as the lowest dB level in which over 95% of test subjects elicited a + response for that value point (frequency). This is a table of pulsed pure tone sounds, each of which is a measured dB relative to the SBS throughout the range of test frequencies described above in 3 and 4. The high frequency limit will be that defined by the sound card limit of the determined universe of sound cards for which compatibility is desired, and will be around 12,000 hz. Between 8,000 and 12,000 hz three test increments will be determined based on 8,000 hz being the starting test point, the test limit determined as described above, and a frequency test point bisecting the starting and ending high frequency test points.

6. A second test, called an Audiometric sound discrimination test (ASD) is performed using the white noise probe as background, and then retesting the TOV frequencies. The white noise background that will become the standard for this test can be selected within a wide range, the preference being is selected at a level the majority of test subjects define as the loudest which can be heard without discomfort or seeming to be unpleasant. This baseline will be determined and varied by age. A new TOV will be determined by retesting the original test population with pulsed frequencies in the presence of this noise and determining the lowest dB value that is heard by 95% of test subjects, again stratified by age and tested throughout the frequency range to determine this table.

7. Two tests will therefore further define the hearing test of the present invention: a pure tone test set based on the SBS; and an ASD test defined by the presence of a continuous background noise. Each test will present a predetermined frequency dB value that for age 95% of normals identified, according to the TOV for age. It will then increase by 10 dB relative to this starting value until a positive response is elicited. This will be repeated twice for each test frequency tested with each test. Failure to respond will elicit another test stimulus at a higher dB value of about 10–25 dB, to be determined based on the test range of normals, such that the increment of change is sufficient to allow 100% of test subjects to identify the test sound dB. The dB increment increase, to be determined, along with the TOV for each test, will constitute the testing algorithm.

8. A high, borderline, low, very low sensitivity screening result will be determined based on comparison with patients with early, moderate and high levels of hearing loss at the different test frequencies. Either % score or a derived calculation from comparison of the pure tone and ASD test will be used to refine the screening labels of high to low hearing sensitivity (or loss using the converse). As the number of test takers tested with corresponding professional Audiometric scores increases the test analysis algorithm can be further refined to modify sensitivity and specificity, as well as allow for a % likelihood value of hearing loss as analysis output, in addition to the screening pass-fail scoring and detailed relative quantitative dB loss vs. frequency analysis.

Invention in General

The self-administered test of the invention can quickly analyze hearing simply by having the user enter a computer system accessible to a community of users such as the world wide web of the internet. The user enters the web site name which presents a screen to the user. A web-site screen preferably presents questions to the user which would include information to identify the user (e.g. user name and social security number) and the user's age in that hearing ability is generally age related. After entering requested background information the user is instructed to provide a surrounding environment with no background sound or a barely discernable background sound.

At this point the test can be administered in a variety of different ways. First, the test cab be administered using only speakers connected to the user's computer. There are several different embodiments of this aspect of the invention as explained below. Second, the test can be administered using earphones which may be standardized hearphones specifically designed for use with the test. The use of earphones can greatly simplify the invention. However, many users will not take the test if the use of earphones is required. Thus, the present invention provides a means for taking the test without the need of any equipment beyond a standard PC, sound card, keyboard, and preferably a mouse and monitor screen. When only such minimal equipment is used the number of users who will access and take the test is dramatically increased.

When speakers and not earphones generate the sounds it is necessary to go through certain procedures to establish a standard for the user's system. To do this the user is instructed to cover a non-test ear, e.g. using moderate pressure via the hand's palm or fingertips to the outer ear canal. Alternately an earplug could also be used. A baseline test tone (BTT) is then presented to the unblocked test ear. At this point interactive responses are required to determine a relative 0 dB HL baseline (described further below).

Once the 0 dB HL baseline has been established the computer system initiates a test program whereby data is sent to the user's computer which data instructs the user's computer to generate a sequence of pure tones. The tones generated are preferably pulsed tones of a relatively short duration, e.g. under 1 second or more preferably under 0.1 second. The tones are preferably intermixed with periods of non-testing silence. The tones which are presented to the user are selected from a pre-determined table of values (TOV) that is age matched at the specific test frequencies of each of the sounds generated.

The test tones are presented to the user at a predetermined relative dB value to the baseline 0 dB HL. The user may hit any key on the keyboard or click the mouse to indicate that the user has detected the sound generated by the user's computer. Each of the user's responses (e.g. mouse clicks) during the intermixed silence are scored as a measurement of compliance, i.e. test-taking accuracy. The tones of the upper limit of testing volume are periodically interspersed, as well, to test for expected mouse clicks and confirm understanding and compliance with test instructions. The testing is repeated with a modified TOV developed for presentation of background sound simultaneous with pure tone presentation. By repeating the testing in this manner and crossing the results obtained with those obtained in the initial testing it is possible to further verify the accuracy of the test on the particular user.

The results of the testing are recorded and an analysis algorithm is used to determine a result which can be presented to the user and the user's caretaker. The results may be presented in terms of a past-fail-borderline score overall or for each level of the frequency. The test results presented may be more refined and provide a high-borderline-low-very low sensitivity result. It is preferable for the results to provide detailed relative quantitative analysis of dB loss versus frequency. The test program is repeated with incremental increases in dB values at frequencies where the user did not provide a response to a sound generated. In this manner it is possible to determine the dB level at which the user can respond at that particular frequency.

Minimizing System Variables

The users will access the test with a range of different PC's and the PC's will have different sound cards, settings, and speakers. Further, the user's environment will have different levels of background noise. These and other variables should be minimized to improve the accuracy of the results obtained. The present invention provides two basic means for minimizing such variables.

In a first method, one or more sound probes are sent to the user and the user indicates when the sound can not be heard, i.e. the sound is at a detected 0dB level. This can be obtained by sending the user a series of sounds at the same frequency but at continually decreasing amplitude until the sound is no longer heard or just barely heard by the user—this is the detected 0dB level. Another series of sounds at a different frequency can be sent to establish another 0dB level and this can be done at a plurality of different frequencies or for only one or a known group of different frequencies. If a user has hearing loss, that loss is generally more profound at certain frequencies. It is preferable to establish the detected 0dB level at a frequency where the user does not have significant hearing loss. The detected 0dB level can also be established by the user continually and gradually adjusting the amplitude of the sound received to an undetectable or barely detectable level, i.e. the level of sound sent to the user remains at the same frequency and amplitude, but the user adjusts components such as the speakers until the level is undetectable or barely detectable. Establishing the detected 0dB level is done separately with each ear. Once the detected 0dB level is established the test can be carried out with a degree of confidence that system and environment variables have been minimized.

In a second method of minimizing variables a background sound probe is used. The background sound probe is a multifrequency sound which generates frequencies across the band of frequencies normally heard by a human. The background sound can be referred to a "white noise" and can be set individually based on the detectable 0dB level as explained above or can be set at an arbitrary level, e.g. in a range from about 10% to about 75% of the maximum tolerable sound level. The background sound may be set at a level in a range from 10% to 75% of the maximum level which can be obtained by the user's system. When generating the background noise the user's hearing is tested by determining the user's ability to detect sounds over the background sound.

This latter test allows for assessment of overall discrimination while stressing this system, enabling more accurate determination of those with generalized hearing loss where ability to selectively isolate background from other specific frequencies is typically reduced.

As a result of these two advances a much more consistent and accurate hearing test for both selective frequency loss and general hearing loss is possible on PC systems simply using the downloadable or online software of the current invention.

Establishing a Table of Values (TOV)

A TOV 1 is established based on testing of age-matched audiometrically tested normal individuals at frequencies in a range of 500 hv to about 12,000 hv. The testing is carried out relative to a 0 dB HL established for each test taker. Testing is preferably carried out at least at 500, 1,000, 2,000, 4,000, 6,000, 8,000, 9,500, and 11,000 hz. The table of values is generated by presenting a single tone of the lowest dB value selected for each frequency to be tested based on an epsilon 1 statistical probability of normal (normal for 95% or more of the individuals tested). Each TOV 1 is for a specified time and duration, which is constant for a given frequency, but may be varied by frequency as well as age. Although the TOV values using more than a 1-second duration pulse may be used it is preferable for the TOV values to be generated using pulses of less than one second and more preferably less than 0.1 second. The TOV pulse duration may increase to allow the greatest statistical correlation with age and determination of the best low threshold tone for each frequency at that age.

Those skilled in the art will recognize that a variety of different procedures could be utilized to establish a baseline TOV and as such it could be used with the present invention. Further, those skilled in the art will recognize that the internet hearing testing system of the present invention could be carried out using other mechanisms for standardizing the sound values generated by each user's individual computer. For example, it would be possible to carry out the test in a simpler manner if each user were supplied with a standard known set of earphones. With these earphones the sounds being generated to the earphones would be known and the user's hearing could be tested in a much simpler manner. However, in many instances it is difficult for users to obtain earphones and many potential users would not use the test if required to purchase or otherwise obtain the earphones prior to testing. Further, even with the earphones in place some standard values generated with respect to users being tested with those earphones would be necessary. Further, it would be necessary for the system which administers the test to determine a particular sound card being used by the users computer and to adjust the system based on that particular sound card.

Another manner of carrying out the invention with or without earphones would be to have each user present sounds generated by the speaker or earphone speakers to the receiver of the user's telephone and have the sound sent back to the computer system generating the test. In this manner it would be possible to determine aspects of the sound being generated and adjust the test results accordingly. In yet another embodiment the user could make use of a sound detection device which device would provide a reading of both frequency and decibel levels. Those readings could be automatically and electronically sent back to the computer generating the test or could be entered by the user after sounds were generated by the user's computer. All of these alternative methods would offer some degree of improved sophistication of the test but all are less desirable in that they all require the use of additional components and would therefore decrease the likelihood of large numbers of users taking the test.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of determining an amplitude for a background tone for self-administration of a hearing test via a computer system, comprising the steps of:

sending data to a user's computer which data prompts the computer to generate a background sound covering a plurality of frequencies over a range detectable by a human ear;

increasing the amplitude of the background sound to within a range of about 10% to about 75% of the maximum sound which a sound system of the user's computer is capable of generating;

sending additional data to the user's computer which prompts the computer to generate a series of sounds which sounds are detectable, to a human with normal hearing, above the background sound;

receiving and analyzing responses to the series of sounds to provide information on the user's hearing.

* * * * *